(12) United States Patent
Conn et al.

(10) Patent No.: US 6,561,978 B1
(45) Date of Patent: May 13, 2003

(54) DEVICES AND METHODS FOR FREQUENT MEASUREMENT OF AN ANALYTE PRESENT IN A BIOLOGICAL SYSTEM

(75) Inventors: Thomas E. Conn, Palo Alto, CA (US); Russell Ford, Portola Valley, CA (US); Russell O. Potts, San Francisco, CA (US); Pravin L. Soni, Sunnyvale, CA (US); Janet A. Tamada, Mountain View, CA (US); Michael J. Tierney, San Jose, CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

(21) Appl. No.: 09/503,227

(22) Filed: Feb. 11, 2000

Related U.S. Application Data

(60) Provisional application No. 60/119,918, filed on Feb. 12, 1999.

(51) Int. Cl.[7] ................................................. A61B 5/00
(52) U.S. Cl. ........................ 600/309; 600/365; 600/347
(58) Field of Search ............................... 600/345–347, 600/354–365, 310, 309, 322–326, 316; 128/903–904; 604/93.01

(56) References Cited

U.S. PATENT DOCUMENTS

| | | | |
|---|---|---|---|
| 4,178,916 A | | 12/1979 | McNamara |
| 4,509,531 A | | 4/1985 | Ward |
| 4,703,756 A | | 11/1987 | Gough et al. |
| 5,062,841 A | | 11/1991 | Siegel |
| 5,063,081 A | * | 11/1991 | Cozzette et al. ............... 435/4 |
| 5,077,753 A | | 12/1991 | Grau, Jr. et al. |
| 5,112,614 A | | 5/1992 | Magruder et al. |
| 5,113,869 A | * | 5/1992 | Nappholz et al. ........... 600/508 |

(List continued on next page.)

FOREIGN PATENT DOCUMENTS

| | | |
|---|---|---|
| EP | 0 942 278 A2 | 9/1999 |
| WO | WO 91/12772 | 9/1991 |
| WO | WO 95/02357 | 1/1995 |
| WO | WO 96/00109 | 1/1996 |
| WO | WO 96/00110 | 1/1996 |
| WO | WO 96/36134 | 11/1996 |
| WO | WO 97/02811 | 1/1997 |
| WO | WO 97/10356 | 3/1997 |
| WO | WO 97/10499 | 3/1997 |
| WO | WO 97/24059 | 7/1997 |
| WO | WO 98/42252 | 10/1998 |
| WO | WO 99/40848 | 8/1999 |
| WO | WO 99/58050 | 11/1999 |
| WO | WO 99/58051 | 11/1999 |
| WO | WO 99/58190 | 11/1999 |
| WO | WO 99/58973 | 11/1999 |
| WO | WO 00/47109 | 8/2000 |

OTHER PUBLICATIONS

Webster's II new Riverside University Dictionary, The Riverside Publishing Company, 1994, p. 970.*

Freiherr, "Wireless, Technologies Find Niche in Patient Care," *Medical Device and Diagnostic Industry* pp. 83–93 (1998).

Tamada et al., "Noninvasive Glucose Monitoring," *JAMA* 282:1839–1844 (1999).

*Primary Examiner*—Eric F. Winakur
*Assistant Examiner*—Matthew Kremer
(74) *Attorney, Agent, or Firm*—Barbara G. McClung; Gary R. Fabian

(57) ABSTRACT

Devices and methods are provided for frequently measuring the concentration of an analyte present in a biological system. A monitoring system having at least two components is employed in order to allow separation of data collection from data processing and display. Such separation allows greater flexibility and convenience for the user.

16 Claims, 12 Drawing Sheets

U.S. PATENT DOCUMENTS

| | | | |
|---|---|---|---|
| 5,140,985 A | | 8/1992 | Schroeder et al. |
| 5,279,543 A | | 1/1994 | Glikfeld et al. |
| 5,362,307 A | * | 11/1994 | Guy et al. .................... 604/20 |
| 5,458,140 A | * | 10/1995 | Eppstein et al. ............ 600/573 |
| 5,462,051 A | * | 10/1995 | Oka et al. .................... 600/300 |
| 5,507,288 A | * | 4/1996 | Bocker et al. .............. 600/322 |
| 5,569,186 A | * | 10/1996 | Lord et al. .................... 604/67 |
| 5,636,632 A | | 6/1997 | Bommannan et al. |
| 5,721,783 A | * | 2/1998 | Anderson ................... 381/328 |
| 5,730,714 A | | 3/1998 | Guy et al. |
| 5,735,273 A | | 4/1998 | Kurnik et al. |
| 5,771,890 A | | 6/1998 | Tamada |
| 5,807,375 A | | 9/1998 | Gross et al. |
| 5,827,183 A | | 10/1998 | Kurnik et al. |
| 5,830,132 A | * | 11/1998 | Robinson ................... 600/310 |
| 5,875,186 A | | 2/1999 | Belanger et al. |
| 5,882,300 A | | 3/1999 | Malinouskas et al. |
| 5,897,033 A | | 4/1999 | Okawa et al. |
| 5,914,701 A | * | 6/1999 | Gersheneld et al. ........ 345/156 |
| 5,954,685 A | | 9/1999 | Tierney |
| 5,982,297 A | | 11/1999 | Welle |
| 5,989,409 A | | 11/1999 | Kurnik et al. |
| 5,995,860 A | | 11/1999 | Sun et al. |
| 6,023,629 A | | 2/2000 | Tamada |
| 6,024,699 A | * | 2/2000 | Surwit et al. ................ 600/300 |
| 6,049,727 A | * | 4/2000 | Crothall ....................... 600/310 |
| 6,059,736 A | * | 5/2000 | Tapper ....................... 600/573 |
| 6,134,461 A | | 10/2000 | Say et al. |
| 6,159,147 A | | 12/2000 | Lichter et al. |
| 6,175,752 B1 | | 1/2001 | Say et al. |
| 6,248,067 B1 | * | 6/2001 | Causey, III et al. ........ 600/365 |
| 6,277,067 B1 | * | 8/2001 | Blair .......................... 600/167 |

* cited by examiner

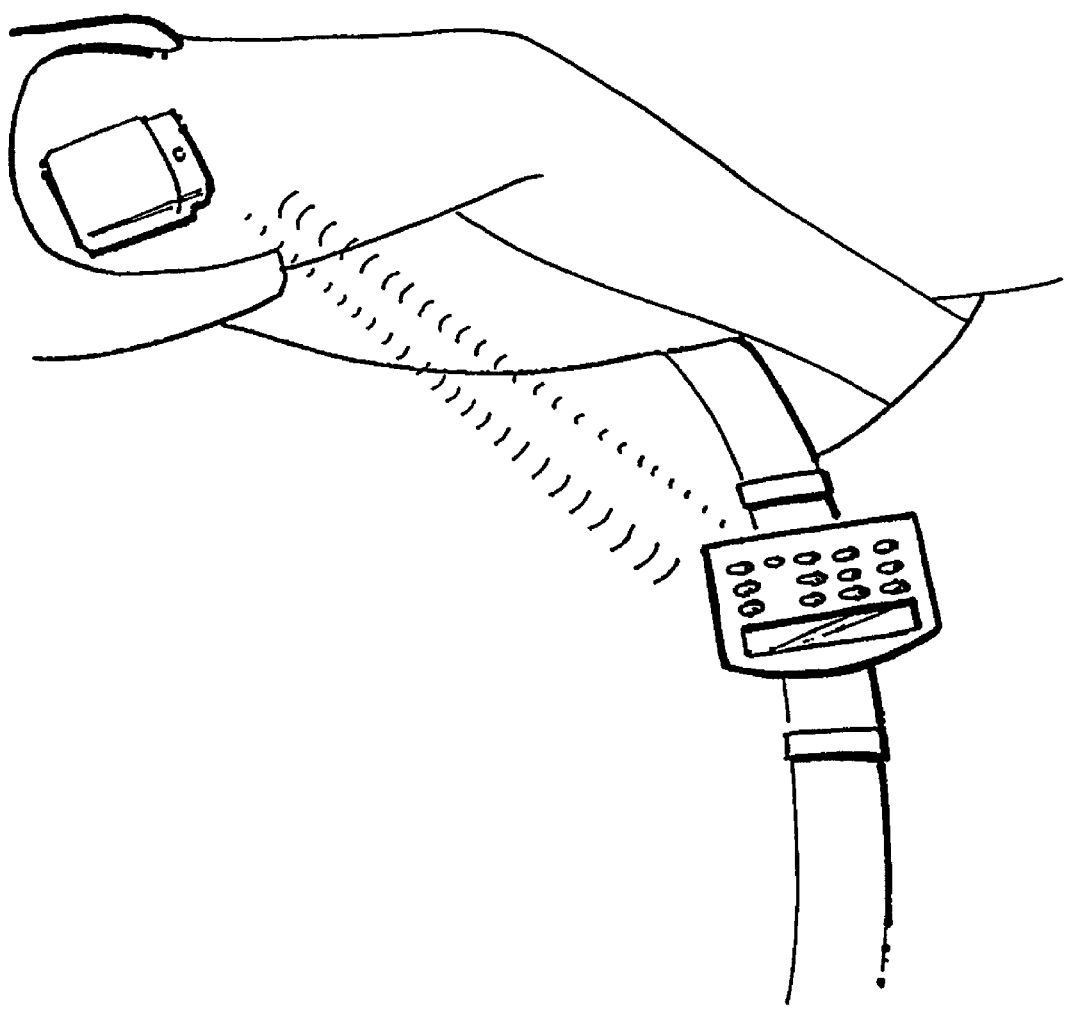

DEVICES AND METHODS FOR FREQUENT MEASUREMENT OF AN ANALYTE PRESENT IN A BIOLOGICAL SYSTEM

CROSS-REFERENCE TO RELATED APPLICATION

This application is related to provisional patent application serial No. 60/119,918, filed Feb. 12, 1999, from which priority is claimed under 35 USC §119(e)(1) and which is incorporated herein by reference in its entirety.

TECHNICAL FIELD

The present invention is in the field of medical devices. More particularly it relates to methods and devices for measuring an analyte present in a biological system.

BACKGROUND

Self-monitoring of blood glucose is a critical part of managing diabetes. However, present procedures for obtaining such information are invasive, painful and provide only periodic measurements. Standard methods of measuring involve the use of painful and cumbersome finger stick blood tests. Thus, development of a painless and automatic approach would represent a significant improvement in the quality of life for people with diabetes. Further, a tight glucose control regimen, which uses frequent glucose measurements to guide the administration of insulin or oral hypoglycemic agents, leads to a substantial decrease in the long-term complications of diabetes. See, Diabetes Control and Complication Trial Research Group (1993) *N. Engl. J. Med.* 329:997–1036.

SUMMARY OF THE INVENTION

In one aspect, the invention includes a monitoring system for frequently measuring an analyte present in a biological system, said monitoring system comprising,
(a) a first component comprising
  (i) a transdermal or transmucosal sampling mechanism for extracting the analyte from the biological system, wherein said sampling mechanism is adapted for extracting the analyte across a skin or mucosal surface of said biological system;
  (ii) sensing mechanism in operative contact with the analyte extracted by the sampling mechanism, wherein said sensing mechanism obtains a signal from the extracted analyte and said signal is specifically related to the analyte; and
  (iii) first mechanism for providing operative communication with a second component of the monitoring system; and
(b) a second component comprising
  (i) a user interface; and
  (ii) second mechanism for providing operative communication with the first component.

In certain embodiments, the sampling mechanism is iontophoresis, electroosmosis, sonophoresis, microdialysis, suction and passive diffusion. In certain embodiments, the first component further comprises a computing mechanism that converts the signal from the extracted analyte to an output indicative of the amount of analyte extracted by the sampling mechanism. The output can be communicated to the second component for display. Further, in other embodiments, the second component receives the signal from the first component, wherein the second component further comprises a computing mechanism that converts the signal from the extracted analyte to an output indicative of the amount of analyte extracted by the sampling mechanism and wherein the second component displays said output. The first and second mechanisms for providing operative communication can comprise a wire-like connection, wireless communication technology or a combination of wire-like and wireless technologies. Wireless communication technology can employ, for example electromagnetic waves (e.g, low frequency electromagnetic waves in a frequency range of about 1 Hz. to about 1 Mega Hz; medium frequency electromagnetic waves in a frequency range of about 1 Mega Hz. to about 500 Mega Hz or high frequency electromagnetic waves in a frequency range of about 500 Mega Hz. to about 5 Giga Hz); capacitance coupling between the biological system and the biological system's environment; inductive coupling; infrared coupling; high frequency acoustic energy or combinations thereof. In still further embodiments, the second component of the monitoring system relays command signals to the first component, for example, signals to control operation of the sensing mechanism or signals to control operation of the sampling mechanism. In certain embodiments, the second component can store analyte-related data. In yet another embodiments, the analyte is glucose. In certain embodiments, the biological system is a mammal, for example a human.

In yet another aspect of the invention, the monitoring system as described herein that further comprises
(c) a third component comprising
  (i) a delivery device; and
  (ii) a third mechanism for providing operative communication with the first and second components. The delivery device can be implanted in the biological system (e.g., subcutaneously) or, alternatively, can be external to the biological system. In certain embodiments, the analyte is glucose and the delivery device comprises an insulin pump. In certain embodiments, the communication between first and second components and the third component is wireless, for example, one or more of the wireless technologies described herein.

In yet another aspect, the invention includes a monitoring system described herein that further comprises
(c) a third component comprising
  (i) a modem or personal computer; and
  (ii) a third mechanism for providing operative communication with the first and second components. In certain embodiments, the modem or personal computer is remote from the biological system and the communication between the first and second components and the third component is wireless. The modem or personal computer may also be operably linked to a wide area network (WAN), for example the internet. In certain embodiments, the analyte is glucose.

These and other embodiments of the present invention will readily occur to those of ordinary skill in the art in view of the disclosure herein.

BRIEF DESCRIPTION OF THE FIGURES

FIGS. 1A to 1L show representative embodiments of a monitoring system of the present invention which has two components.

FIGS. 1A through 1H depict a two component system while

FIGS. 1I through 1L depict a system having three components.

DETAILED DESCRIPTION OF THE INVENTION

Figure 1A:
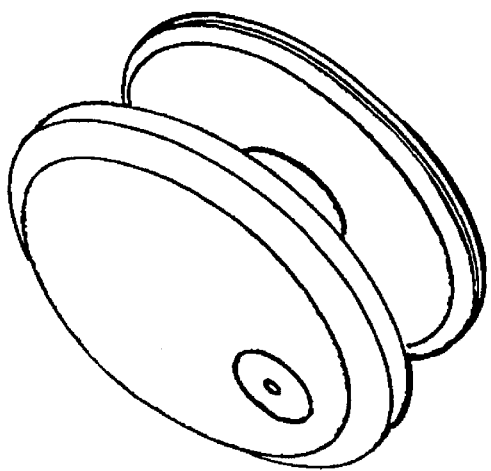
Figure 1A:
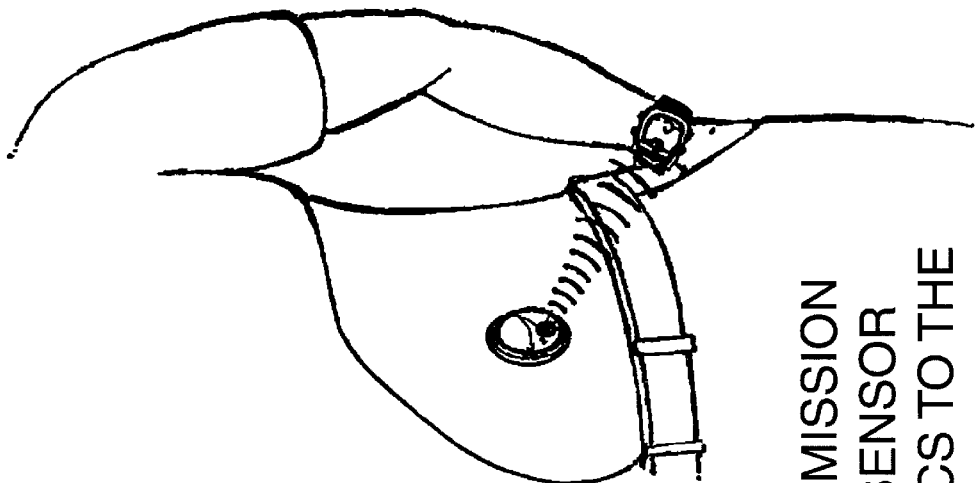

Before describing the present invention in detail, it is to be understood that this invention is not limited to particular formulations or process parameters, as such may, of course, vary. It is also to be understood that the terminology used herein is for the purpose of describing particular embodiments of the invention only, and is not intended to be limiting.

The present invention relates to monitoring systems generally used for extracting small amounts of a target analyte from the biological system, and then sensing and/or quantifying the concentration of the target analyte. Unlike previous devices, the sampling/sensing mechanism and user interface are found on separate components. Thus, the present invention relates to a monitoring system with at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of sampling/sensing, different aspects of data manipulation or recording) are found in both components. Alternatively, microprocessing components may be located in one or the other of the at least two components. The second component of the monitoring system can assume many forms, including, but not limited to, the following: a watch, a credit card-shaped device (e.g., a "smart card" or "universal card" having a built-in microprocessor as described for example in U.S. Pat. No. 5,892,661), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, an insulin delivery unit (e.g., insulin pump) is included in the system. Insulin delivery units, both implantable and external, are known in the art and described, for example, in U.S. Pat. Nos. 5,995,860; 5,112,614 and 5,062,841. Preferably, when included as a component of the present invention, the insulin delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small watch, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. In preferred embodiments, the mechanism for providing operative communication between the two components is wireless. FIGS. 1A to 1H show exemplary embodiments of monitoring systems having two components. FIGS. 1I to 1L show exemplary embodiments of monitoring systems having three components. These exemplary embodiments are described in further detail below.

All publications, patents and patent applications cited herein, whether supra or infra, are hereby incorporated by reference in their entirety.

I. Definitions

It must be noted that, as used in this specification and the appended claims, the singular forms "a", "an" and "the" include plural referents unless the content clearly dictates otherwise. Thus, for example, reference to "a binder" includes a mixture of two or more such binders, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism" or "sampling system" refers to any device for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. As used herein, the term "sampling" mechanism refers to extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling mechanism are in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis, suction, electroporation, thermal poration, passive diffusion, microfine (miniature) lances or cannulas, subcutaneous implants or insertions, and laser devices. Iontophoretic sampling devices are described, for example, in International Publication No. WO 97/24059, published Jul. 10, 1997; European Patent Application EP 0942 278, published Sep. 15, 1999; International Publication No. WO 96/00110, published Jan. 4, 1996; International Publication No. WO 97/10499, published Mar. 2, 1997; U.S. Pat. Nos. 5,279,543; 5,362,307; 5,730,714; 5,771,890; 5,989,409; 5,735,273; 5,827,183; 5,954,685 and 6,023,629, all of which are herein incorporated by reference in their entireties. Sonophoresis uses ultrasound to increase the permeability of the skin (see, e.g., Menon et al. (1994) *Skin Pharmacology* 7:130–139). An exemplary sonophoresis sampling system is described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov.20, 1997); and WO 97/43962 (published Nov.27, 1997). Laser devices use a small laser beam to create one or more micropores in the uppermost layer of the patient's skin (see, e.g., Jacques et al. (1978) *J. Invest. Dermatology* 88:88–93; International Publication WO 99/44507, published Sep. 10, 1999; International Publication WO 99/44638, published Sep. 10, 1999; and International Publication WO 99/40848, published Aug. 19, 1999.

The term "collection reservoir" is used to describe any suitable containment mechanism for containing a sample extracted from a biological system. For example, the collection reservoir can be a receptacle containing a material which is ionically conductive (e.g., water with ions therein), or alternatively, it can be a material, such as, a sponge-like material or hydrophilic polymer, used to keep the water in place or to contain the water. Such collection reservoirs can be in the form of a hydrogel (for example, in the form of a disk or pad). Hydrogels are typically referred to as "collection inserts." Other suitable collection reservoirs include, but are not limited to, tubes, vials, capillary collection devices, cannulas, and miniaturized etched, ablated or molded flow paths.

A "housing" for the sampling system can include suitable electronics (e.g., microprocessor, memory, display and other circuit components) and power sources for operating the sampling system in an automatic fashion.

A "monitoring system," as used herein, refers to a system useful for frequently measuring a physiological analyte present in a biological system. Such a system typically includes, but is not limited to, sampling mechanism, sensing mechanism, and a microprocessor mechanism in operative communication with the sampling mechanism and the sensing mechanism. As used herein, the term "frequent measurement" intends a series of two or more measurements obtained from a particular biological system, which measurements are obtained using a single device maintained in operative contact with the biological system over the time period (e.g, second, minute or hour intervals) in which the series of measurements is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, whether male or female, are intended to be covered.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any sampling method, which entails extracting and/or transporting an analyte from beneath a tissue surface across skin or mucosal tissue. The term thus includes extraction of an analyte using iontophoresis (reverse iontophoresis), electroosmosis, sonophoresis (see, e.g., U.S. Pat. No. 5,636,632), microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example, by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode), as described for example in U.S. Pat. Nos. 5,771, 890 and 6,023,629.

The term "reverse iontophoresis" refers to the movement of a substance from a biological fluid across a membrane by way of an applied electric potential or current. In reverse iontophoresis, a reservoir is provided at the tissue surface to receive the extracted material, as used in the Gluco Watch® (Cygnus, Inc., Redwood City, Calif.) glucose monitor (See, e.g., Tanada et al. (1999) *JAMA* 282:1839–1844).

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing mechanism," or "biosensor device" encompasses any device that can be used to measure the concentration of an analyte, or derivative thereof, of interest. Preferred sensing devices for detecting blood analytes generally include electrochemical devices, optical and chemical devices and combinations thereof.

Examples of electrochemical devices include the Clark electrode system (see, e.g., Updike, et al., (1967) *Nature* 214:986–988), and other amperometric, coulometric, or potentiometric electrochemical devices. Examples of optical devices include conventional enzyme-based reactions as used in the Lifescan® (Johnson and Johnson, New Brunswick, N.J.) glucose monitor (see, e.g., U.S. Pat. No. 4,935,346 to Phillips, et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors are described by Newman, J. D., et al.(1995) *Analytical Chemistry* 67:4594–4599.

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof, (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect mechanism that the symptoms of the subject being treated are prevented or alleviated. For example, a physiological effect would be one that results in the prolongation of survival in a patient.

The terms "collection assembly," as used herein, refers to any structure that can be used to collect the analyte of interest. Similarly, an "autosensor assembly" refers to any structure capable of sensing the analyte of interest. The structures may be comprised of several layers, for example, a collection reservoir, a mask layer, liners and/or a retaining layer where the layers are held in appropriate, functional relationship to each other. The autosensor assembly may also include liners. Exemplary collection assemblies and autosensor structures are described, for example, in International Publication WO 99/58190, published Nov.18, 1999; and U.S. Pat. Nos. 5,735,273 and 5,827,183.

"Substantially planar" as used herein, includes a planar surface that contacts a slightly curved surface, for example, a forearm or upper arm of a subject. A "substantially planar" surface is, for example, a surface having a shape to which skin can conform, i.e., contacting between the skin and the surface.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

The term "user interface" refers to any means or mechanism that interacts (e.g., provides or exchanges information) with any one of a user's senses. Non-limiting examples of suitable interfaces include visual displays (e.g., LCD displays); tactile or mechanical signals (e.g., vibrations, alarms, buttons, etc.) and auditory signals (e.g., alarm or speaker). The term "microprocessor" refers to any type of device that functions as a microcontroller and also includes any type of programmable logic, for example, Flexible Program Gate Array (FPGA).

As used herein, the term "wire-like" refers to communications involving the transport of signals from one location to another using a wire, cable or other solid object. Examples include the transport of electric charge and/or voltage on metallic wires and the transport of light energy on fiber optic cables. The term "wireless" refers to communications involving the transport of signals from one location to another without the use of wires or cables. Examples include, but are not limited to: the transport of signals through space via electromagnetic waves; the transport of signals through air via pressure waves (e.g., acoustic signals); the transport of signals through space via magnetic fields; the transport of signals through space via electric fields; and combinations of one or more of the foregoing. The term "transceiver" refers to any device which is capable of functioning as both a transmitter and a receiver of signals. An integrated transceiver system is described, for example, in U.S. Pat. No. 5,930,686.

II. General Overview

The present invention is based on the novel concept of separating an analyte monitoring system into at least two components. The first component samples (extracts) and senses (detects) the analyte of interest while the second component includes a user interface. Data processing on the analyte data can be performed by the first component, the second component or both. Additional components, for example, an alarm or a drug delivery unit, can also be included. Particular components of the subject invention are described below. It is to be understood that the various forms of different embodiments of the invention may be combined.

Thus, the present invention relates to a monitoring system, for frequently measuring an analyte present in a biological system, comprising a measurement unit (e.g., sampling mechanism and sensing mechanism) in operative communication with a second component (e.g., a user interface). Further components can be included in the system as well, for example, a third component having display mechanism (display unit), a delivery unit and/or electronic file data serving mechanism. Providing such a system in at least two parts imparts greater flexibility and convenience to the user. In one embodiment, the communication connection between the components can be a wire-like connection (e.g., a wire or multi-wire cable). In a preferred embodiment, operative communications between the components is a wireless link, i.e. provided by a "virtual cable," for example, a telemetry link. This wireless link can be uni- or bidirectional between the two components. In the case of more than two components, links can be a combination of wire-like and wireless.

This monitoring system comprising at least two components relays biosensor information from the measurement unit to the user interface for subsequent analysis and display. It can also relay command signals and information from the user interface to the measurement unit in order to control sensing (e.g., the biosensor) and sampling (e.g., iontophoresis) functions; data processing (e.g., calibration values); and event logging (e.g., meals, exercise, etc.). In some embodiments, additional components, for example, an insulin delivery unit can be included. The insulin delivery unit can receive commands from the measuring system and deliver suitable amounts of insulin.

III. Sampling Mechanism and Sensing Mechanism

The monitoring system of the present invention comprises at least two both sampling and sensing mechanism and, optionally, a power source and a controller (microprocessor). In one aspect, the sampling/sensing mechanism is placed on the skin, e.g., for example for transdermal or transmucosal sampling/sensing. Alternatively, one or more aspects of the sampling/sensing mechanisms can be implanted, for example, subcutaneously into a user. In a preferred embodiment, the sampling mechanism can comprise sampling (e.g., iontophoretic) electrodes that are used to perform frequent transdermal or transmucosal sampling of an analyte of interest (e.g., glucose). The sensing mechanism can comprise biosensor electrodes (see, e.g., European Patent Application EP 0942 278, published Sep. 15, 1999). The sensing mechanism is typically in operative contact with the extracted analyte and obtains a signal from the extracted analyte. The signal is specifically related to the analyte. Thus, the first component provides the mechanism to sample and sense the presence of an analyte, for example by detecting electrochemical signals produced at the biosensor electrode surfaces. Consumable collection assemblies that provide sampling and sensing functions are described, for example in International Publication WO 99/58190, published Nov. 18, 1999.

A. Analytes

The analyte to be monitored by the invention described herein can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate/lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. In preferred embodiments, the analyte is a physiological analyte of interest, for example glucose, or a chemical that has a physiological action, for example a drug or pharmacological agent.

In one embodiment, the analyte is detected by specific enzyme systems. For example, in the case of glucose, the enzyme glucose oxidase catalyzes a redox reaction which produces hydrogen peroxide from glucose and oxygen. A number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine and triglycerides. Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenytion), chemotherapy (e.g., adriamycin), hyperactivity (e.g., ritalin), and anti-organ-rejection (e.g., cyclosporin).

Appropriate formulations of analyte test solutions can be employed and are readily determined by one of skill in the art. For example, test solutions having known concentrations of alcohol, uric acid, cholesterol, or theophylline may be used herein. The solutions may contain additives, diluents, solubilizers, and the like, that do not interfere with detection of the analyte of interest by the sampling system.

Therefore, it is to be understood that, although discussed primary with respect to glucose herein, the present invention is also applicable to the monitoring of other analytes of interest.

B. Sampling Mechanism

Typically, the sampling mechanism is based on transdermal extraction. Measurement and/or sampling with the monitoring system can be carried out in a frequent manner. Frequent measurements allow for closer monitoring of target analyte concentration fluctuations. More specifically, an analyte monitoring system is used to measure changes in analyte levels in an animal subject over a wide range of analyte concentrations. The device can be contacted with the biological system for extended periods of time, and automatically obtains frequent glucose samples in order to measure glucose concentration at various selected intervals.

Sampling is carried out by extracting an analyte (e.g., glucose) through the skin of the patient. It is to be understood that extraction of the analyte can be conducted using a variety of methods, for example, iontophoresis, sonophoresis, suction, electroporation, thermal poration, passive diffusion, microfine (miniature) lances or cannulas, subcutaneous implants or insertions, laser devices and other methods known to those of skill in the art. In one aspect, an iontophoretic current is applied to a surface of the skin of a subject. When the current is applied, ions or charged molecules pull along other uncharged molecules or particles such as glucose which are drawn into a collection reservoir placed on the surface of the skin. The collection reservoir may comprise any ionically conductive material and is preferably in the form of a hydrogel which is comprised of a hydrophilic material, water and an electrolyte.

In one aspect, the sampling device can operate in an alternating polarity mode necessitating the presence of first and second bimodal electrodes and two collection reservoirs. Each bi-modal electrode serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode (described below) at which the chemical compound is catalytically converted at the face of the sensing electrode to produce an electrical signal. Alternating polarity is described, for example, in U.S. Pat. No. 5,954,685.

The iontophoresis (e.g., bi-modal) electrode is preferably comprised of Ag/AgCl, described for example in U.S. Pat. No. 5,954,685 and International Publication WO 99/58190. Preferably, the electrodes are formulated using analytical- or electronic-grade reagents and solvents and are provided such that they are not susceptible to attack (e.g., plasticization) by components in the surrounding environment. The electrochemical reaction which occurs at the surface of this electrode serves as a facile source or sink for electrical current. With regard to operation for extended periods of time, Ag/AgCl electrodes known in the art are capable of repeatedly forming a reversible couple which operates without unwanted electrochemical side reactions (which may give rise to changes in pH, and liberation of hydrogen and oxygen due to water hydrolysis).

C. Sensing Mechanism

As noted above, a sensing mechanism for sensing the analyte of interest is also included in the present invention, and can be, for example, based on electrochemical detection techniques. The sensing mechanism obtains a signal from the extracted analyte that is specifically related to that analyte. A variety of sensing mechanism find use in the present invention, for example, in the case of the analyte glucose, the collection reservoir may further contain an enzyme which catalyzes a reaction of glucose to form an easily detectable species. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal).

Suitable biosensor electrodes are described, for example, in EP 0 942 278. In brief, the biosensor electrodes are constructed of any suitable material, for example, platinum and graphite. The sensor element can also include a reference electrode, and a counter electrode, a mask layer; a retaining layer and/or one or more liners. Suitable configurations (e.g., flexibility, shape, degree of sealing, degree of isolation of components, degree of occlusivity, adhesion to target surface and/or electrodes) can be readily determined by the skilled artisan in view of the teachings herein and devices known in the art, for example as described in EP 0 942 278 and WO 99/58190.

In addition, it may be desirable to configure the sampling/sensing mechanisms (or employ measurement techniques) in such a way that the effect of interfering species on the sensor is reduced. As described for example in International Publication WO 99/58051, published Nov. 18, 1999, extraction and sensing of the analyte may be conducted using a measurement sample which selectively favors analyte-specific signal components over signal components due to interfering species, for example by (a) employing a differential signal process which subtracts non-analyte signal components from the analyte signal; (b) employing a delay step which is performed between the sampling (extraction) and sensing steps; (c) employing a selective electrochemical detection process performed during the sensing step; (d) employing a purge step, performed after the sensing step; (e) employing a charge segregation step or (f) any combination of (a) through (e).

The sampling and sensing mechanisms can be combined into one structure. For example, once formulated, the sampling and/or sensing electrode compositions may be affixed to a suitable rigid or flexible nonconductive surface. For example, a silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. (See, e.g., WO 99/58190).

The general operation of an iontophoretic sampling and sensing system is the cyclical repetition of two phases: (1) a reverse-iontophoretic phase, followed by a (2) sensing phase. During the reverse iontophoretic phase, the first bimodal electrode acts as an iontophoretic cathode and the second bimodal electrode acts as an iontophoretic anode to complete the circuit. Analyte (e.g., glucose) is collected in the reservoirs, for example, a hydrogel. At the end of the reverse iontophoretic phase, the iontophoretic current is turned off. During the sensing phase, in the case of glucose, a potential is applied between the reference electrode and the sensing electrode. The chemical signal reacts catalytically on the catalytic face of the first sensing electrode producing an electrical current, while the first bi-modal electrode acts as a counter electrode to complete the electrical circuit.

The reference and sensing electrodes, as well as, the bimodal electrode described above are typically connected to a standard potentiostat circuit during sensing. The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present system, the electrical current measured at the sensing electrode subassembly is the current that is correlated with an amount of chemical signal.

D. Power Source

A power source (e.g., one or more rechargeable and/or nonrechargeable batteries) can be disposed within the first and/or second components of the monitoring system. For example, in embodiments involving iontophoresis, the power source provides sufficient power to apply an electric potential (either direct current or a more complex waveform) between the two iontophoretic (sampling) electrodes such that current flows from the first iontophoretic electrode, through the first conductive medium into the skin or mucosal surface, and then back out through the second conductive medium to the second iontophoretic electrode. The current flow is sufficient to extract substances including an analyte of interest through the skin into one or both of the collection reservoirs. The electric potential may be applied using any suitable technique, for example, the applied current density may be in the range of about 0.01 to 0.5 mA/cm$^2$.

Similarly, during the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signals retained in the reservoir to electrical signals at the catalytic face of the sensing electrode. The power source also maintains a fixed potential at the electrode where, for example, hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

Non-limiting examples of suitable sources of power include printed batteries, film batteries, moldable batteries, coin cell batteries, prismatic batteries, or cylindrical batteries. Printed batteries can be incorporated into the monitoring system, for instance in the first component during printing of the biosensor. In a representative embodiment, the biosensor is printed onto a 0.005 inch thick PET film substrate. The printed battery can be deposited onto this same substrate using similar thick-film print processes. Anode, insulator material, electrolyte, cathode and encapsulant material can be deposited in sequential steps to create the battery. Electrode materials can be deposited in charged states, such as by charging a printing screen during deposition of the electrode layers, thereby avoiding the need to charge the battery after deposition. Alternatively, film batteries can be assembled with the other components of the sampling/sensing device using, for example, Solid State System™ lithium-ion solid polymer rechargeable batteries from Ultralife Batteries Inc., Newark, N.Y. Thin film batteries and moldable batteries from solid electrodes and/or solid electrolytes can also be used, such as the "RHISS" technology from ECR Corporation, Rehovot, Israel. Coin-cell, prismatic, or cylindrical batteries, for example using nickel metal hydride, various lithium, alkaline, zinc-air, chemistnes, may also be used and are commercially available, for example from Panaxonic Industrial, Secaucus, N.J., Varta Batteries Inc., Elmsford, N.Y. It is to be understood that these and other power sources can also be incorporated into the second component to provide the necessary power to run the user interface and/or microprocessing functions contained in the second component. Thus, selection and implementation of a suitable power source can be readily determined by one of skill in the art in view of one or more of the following factors: the method of extraction (sampling), for example, iontophoresis, sonophoresis, etc.; the nature of the user interface; the method of sensing, for example, with biosensor electrodes; manufacturability; energy density; energy capacity; cost; charging time; self-discharging characteristics; environmental concerns; government regulations; safety; and user preference.

III. User Interface

The second component of the at least two component monitoring system comprises a user interface and, typically, one or more controller (microprocessor) functions. Additional components such as suitable electronics (e.g., microprocessing, memory, display and other circuit components), a power source, an alarm and the like can also be included in the user interface. The user interface may provide numerical readouts, other visual indication of analyte concentration (e.g., arrows), or visual instruction actions (e.g., take medication, eat or drink). Buttons on the user interface may provide the ability to supply information needed to calibrate and/or otherwise control the device.

In one aspect, the first component provides the necessary elements to drive the extraction and sensing of the analyte. The sensing electronics then communicate the results (data) of extraction and sensing to the second component (user interface) where microprocessing functions process the data and/or display such data to the user. Algorithms (programs) capable of data manipulation are known to those of skill in the art. Suitable algorithms useful in processing data (e.g., predicting physiological values, signal processing, predicting concentration, and the like) are described, for example, in International Publication WO 99/58973, published Nov. 18, 1999 and International Publication WO 99/58050, published Nov. 18, 1999. In addition, co-pending, co-owned U.S. Ser. No. 09/198,039, filed Sep. 30, 1998, describes how a Mixtures of Experts algorithm can be used predict a concentration of an analyte of interest. Further, it will be apparent that in alternative embodiments, one or more functions of the microprocessor (e.g., data manipulation, calibration, etc.) can be located within the second component.

In another aspect, one or more of the sampling and sensing functions of the first component are controlled by the second component. For example the operation of the sampling device can be controlled by a controller (e.g., a microprocessor with one or more components located in the second component of the monitoring system), which is in operable communication with the sampling electrodes, the sensor electrodes, the power supply, as well as optional temperature and/or conductance sensing elements, a display, and other electronics.

The user interface (second component) may take a variety of configurations, for example, a credit card like device (e.g., "smartcard"), a watch, pager, or cell phone device that includes memory, a display such as a liquid crystal display (LCD) and buttons. The buttons can be used to control what is displayed and record events occurring during use of the product (e.g., meals, exercise, insulin doses). The user interface may also be a remote device such as a personal computer or network.

Turning now to the specific embodiments shown in the Figures, FIG. 1A shows one embodiment of the present invention in which the first component is worn on the torso (next to the skin) and the user interface is worn as a watch. In this embodiment, the first component (sampling/sensing) relays data about the analyte of interest to the second component (user interface) which then displays the data. In this embodiment, the first component includes microprocessing functions that control sampling and sensing and, in addition, can include data processing functions. The data obtained (and/or processed) by the first component is then transmitted via wireless communication (see Section IV below) to the user interface for display.

Figure 1B:
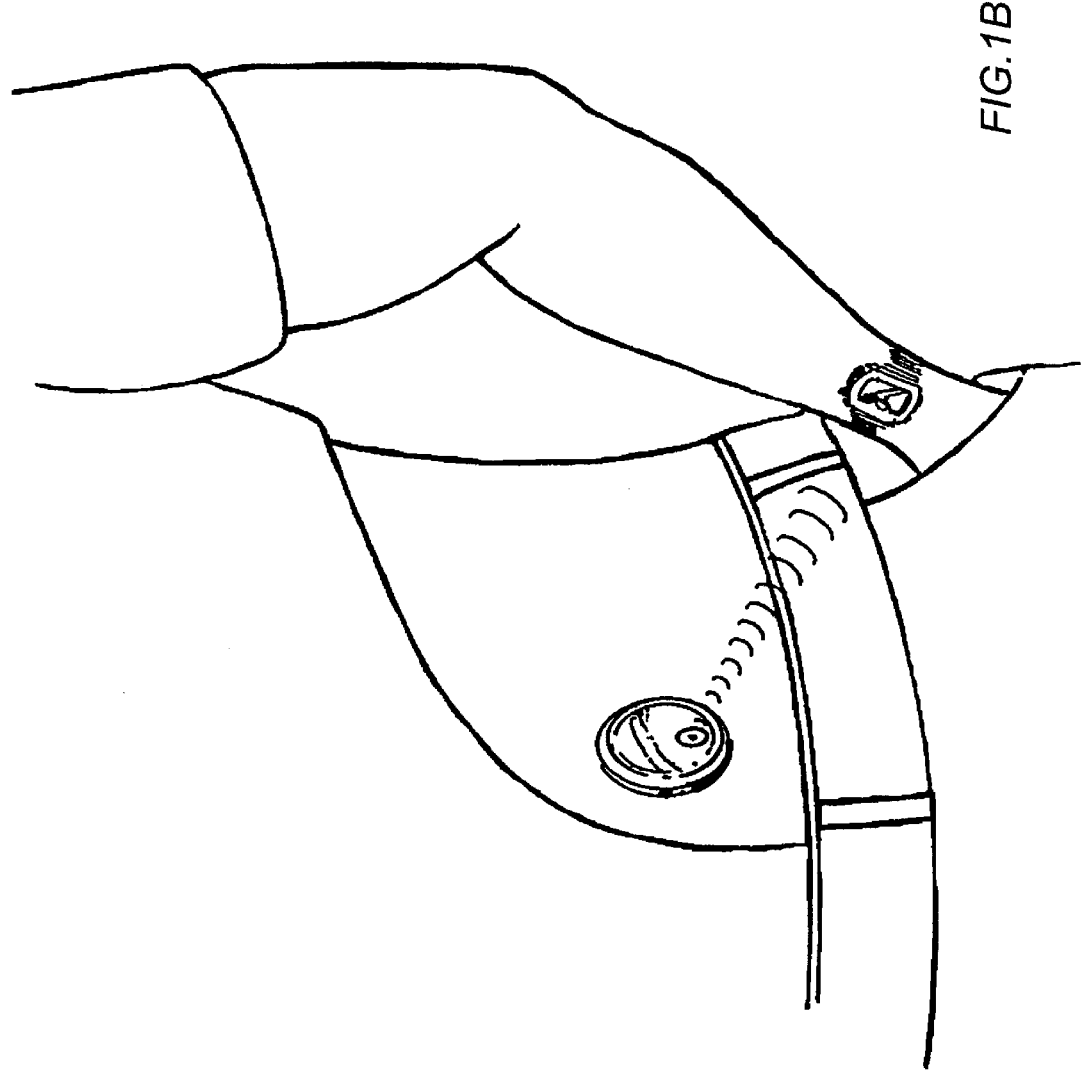

FIG. 1B shows an embodiment similar to that of FIG. 1A where the first component is worn on the torso and the second component takes the form of a watch. In this embodiment, the first component relays information about the analyte to the second component, which contains microprocessing functions (e.g., data processing) and display capabilities.

Figure 1C:
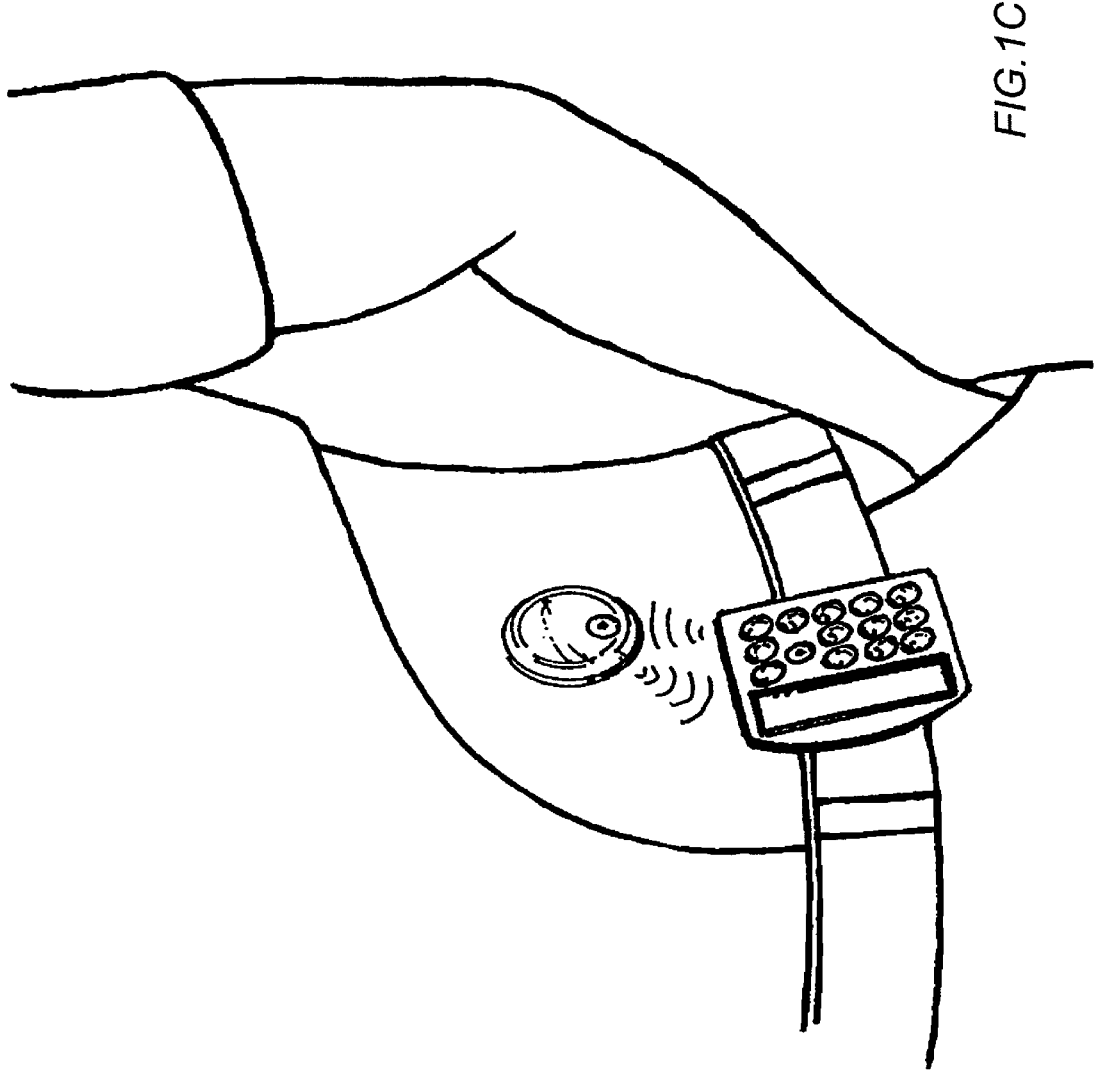

FIG. 1C depicts yet another embodiment where the first component is worn on the torso and the second component is worn as a pager-like device, shown on the belt of the user in FIG. 1C. The second component includes buttons and display panel. Further, the first and second components are in two-way communication with one another. Because of two-way communication, the user has the ability to control the first component with the second component, for example, using the buttons to control collection and sensing intervals and/or data manipulation. The first component will also generally include microprocessing function, for example to control sampling and sensing functions, collect and/or relay data to the second component.

Figure 1D:
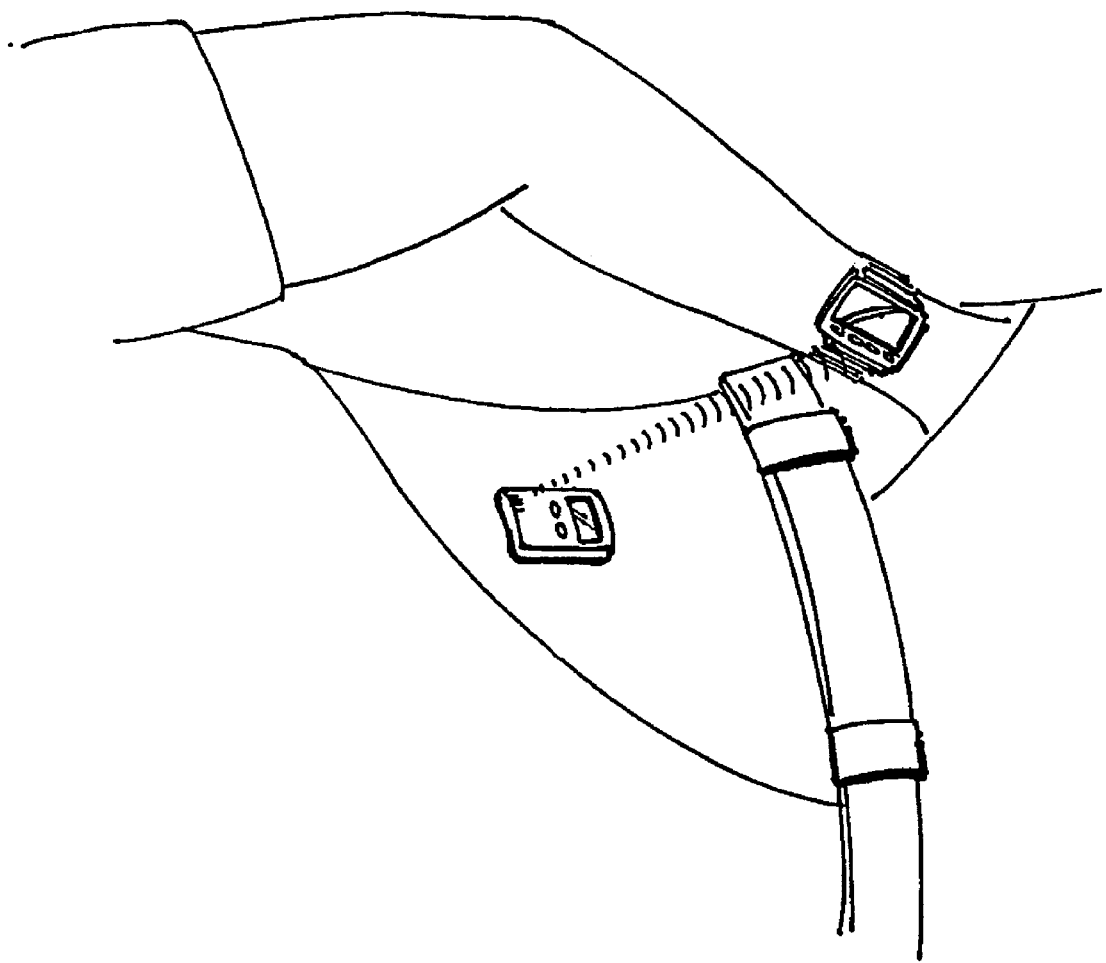

FIG. 1D depicts an embodiment of the present invention in which the first component includes virtually all the microprocessing functions (e.g., control of sampling/sensing, data manipulation, calibration, etc.). The first component is worn next to the skin, for example, under the clothing on the torso. As shown in FIG. 1D, the first component includes a display panel and buttons (e.g., for controlling the microprocessor and/or display). In this embodiment, the first component relays data to the second component for display. The second component is depicted as a watch-like structure and includes a display panel, buttons (e.g., for determining what data is displayed and how it is displayed), and electronics controlling the display.

FIG. 1E depicts yet another embodiment where the first and second components are in two-way communication with one another. The first component is pictured as being worn by the user on the arm and the second component is depicted as a pager-like device on the belt. The second component includes a display panel and buttons. Because the components are in two-way communication, microprocessing functions can be divided between these components in any number of ways. For example, the second component can control the sampling/sensing of the first component (e.g., collection intervals, calibration, etc), receive analyte data from the first component, manipulate and display the analyte data. Further, buttons allow for the user to interface with the monitoring system, for example to control one or more of these aspects. Alternatively, the first component can contain the control functions for sampling/sensing and, optionally, calibration and/or data manipulation. This data can then be transmitted to the second component for further manipulations, if necessary, and display.

Figure 1F:
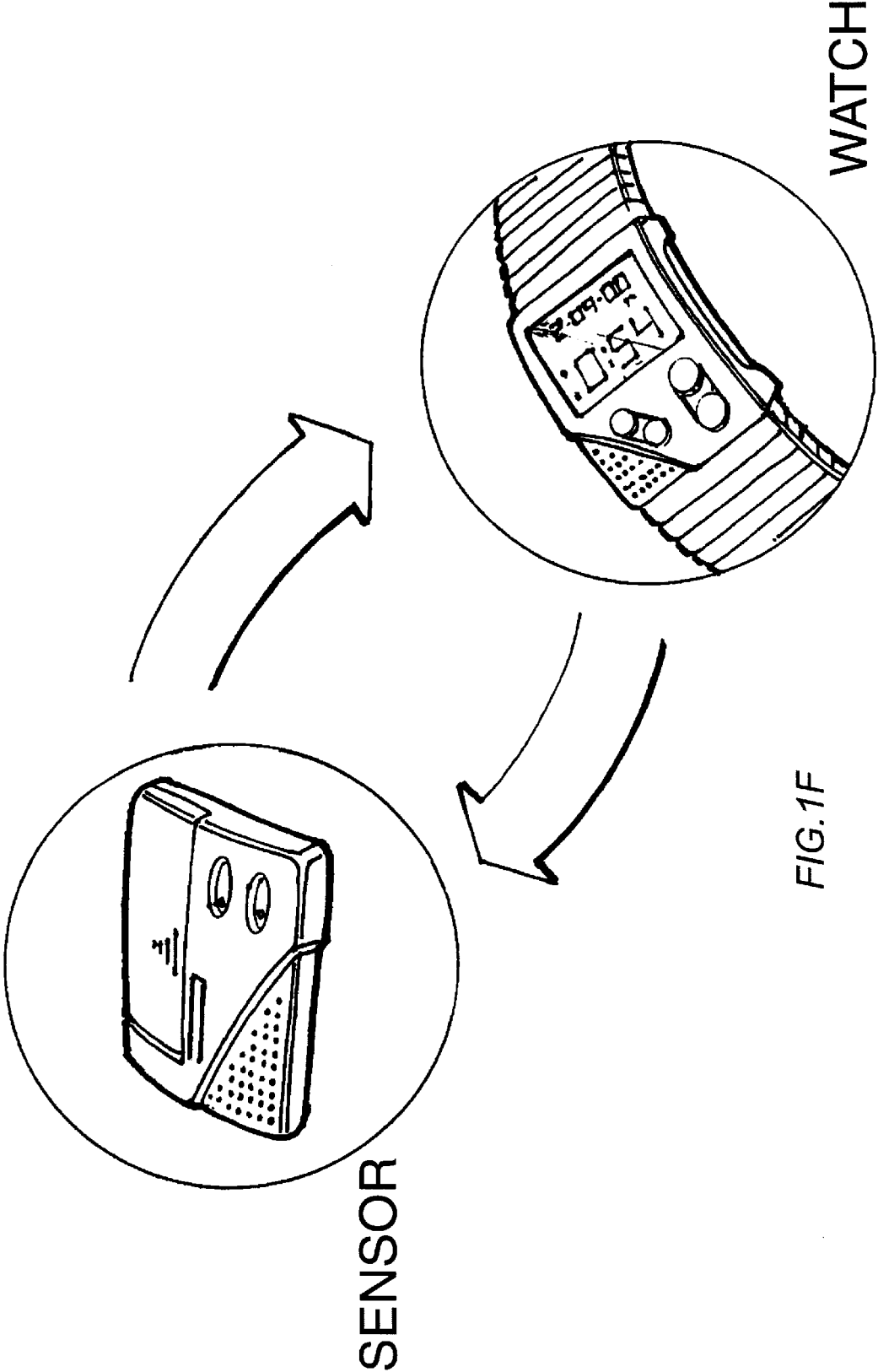

FIG. 1F shows an embodiment of the present invention depicting the two way wireless communication between the first component (labeled "sensor" in the Figure) and the second component (depicted as a watch in the Figure). The user interface includes buttons, microcontroller functions and, in addition, is capable of displaying time, date and analyte data to the user. The sensor will typically be placed next to the skin and the watch worn around the wrist of the user.

Figure 1G:
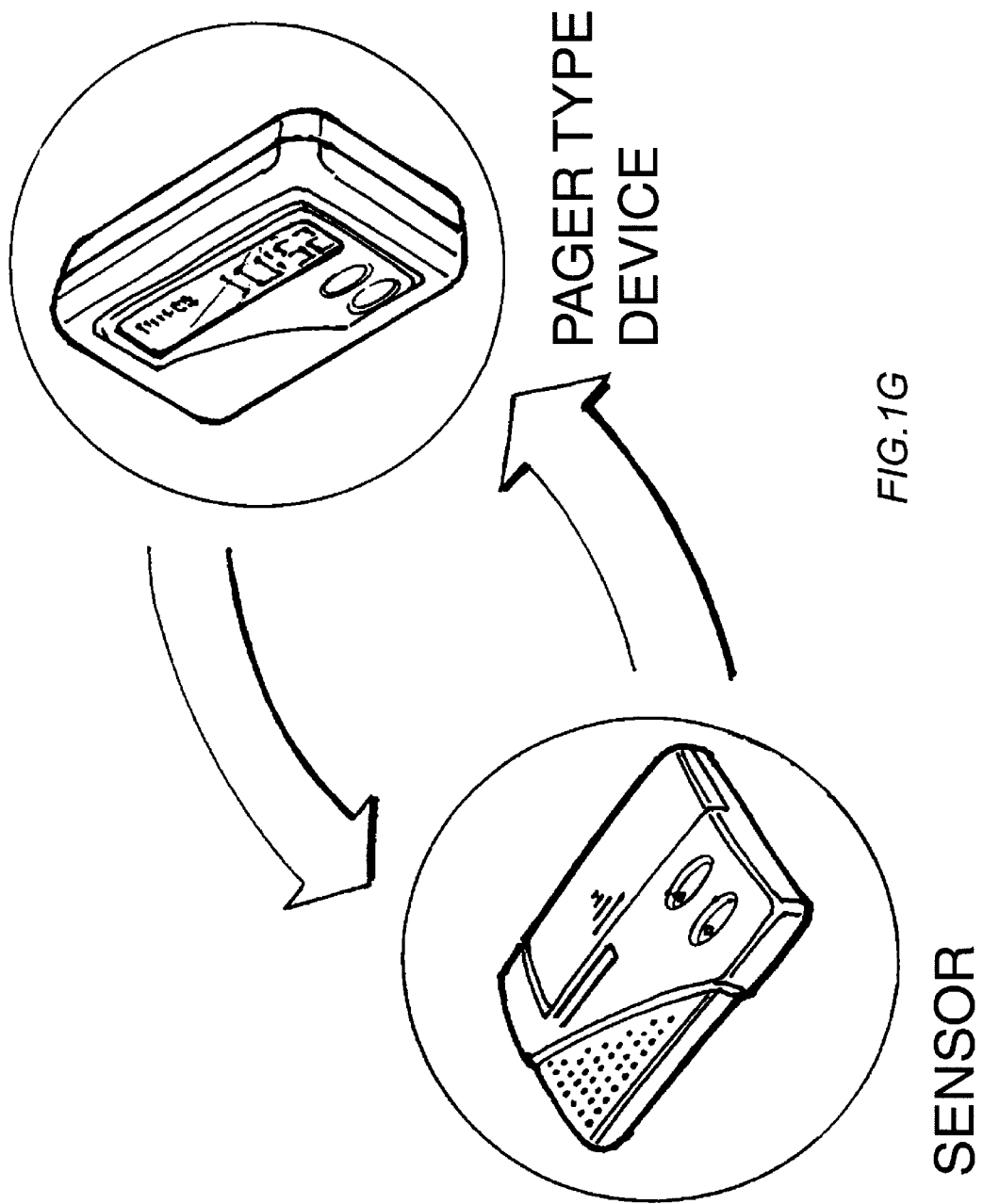

FIG. 1G shows another embodiment having bi-directional wireless communication between the sensor (first component) and user interface (second component), depicted in the Figure as a pager-type device. Similar to the embodiment shown in FIG. 1F, the user interface (e.g., pager-type device) includes buttons, microcontroller functions and, in addition, is capable of visually displaying time, date and analyte data to the user. In some embodiments, the pager-type device will also be capable of sending auditory and/or tactile (e.g., vibrational) signals to the user regarding analyte data, time, etc. The sensor component is typically be placed next to the skin of the user and the pager-type device worn outside the clothes or carried in a purse, bag, briefcase or the like.

Figure 1H:
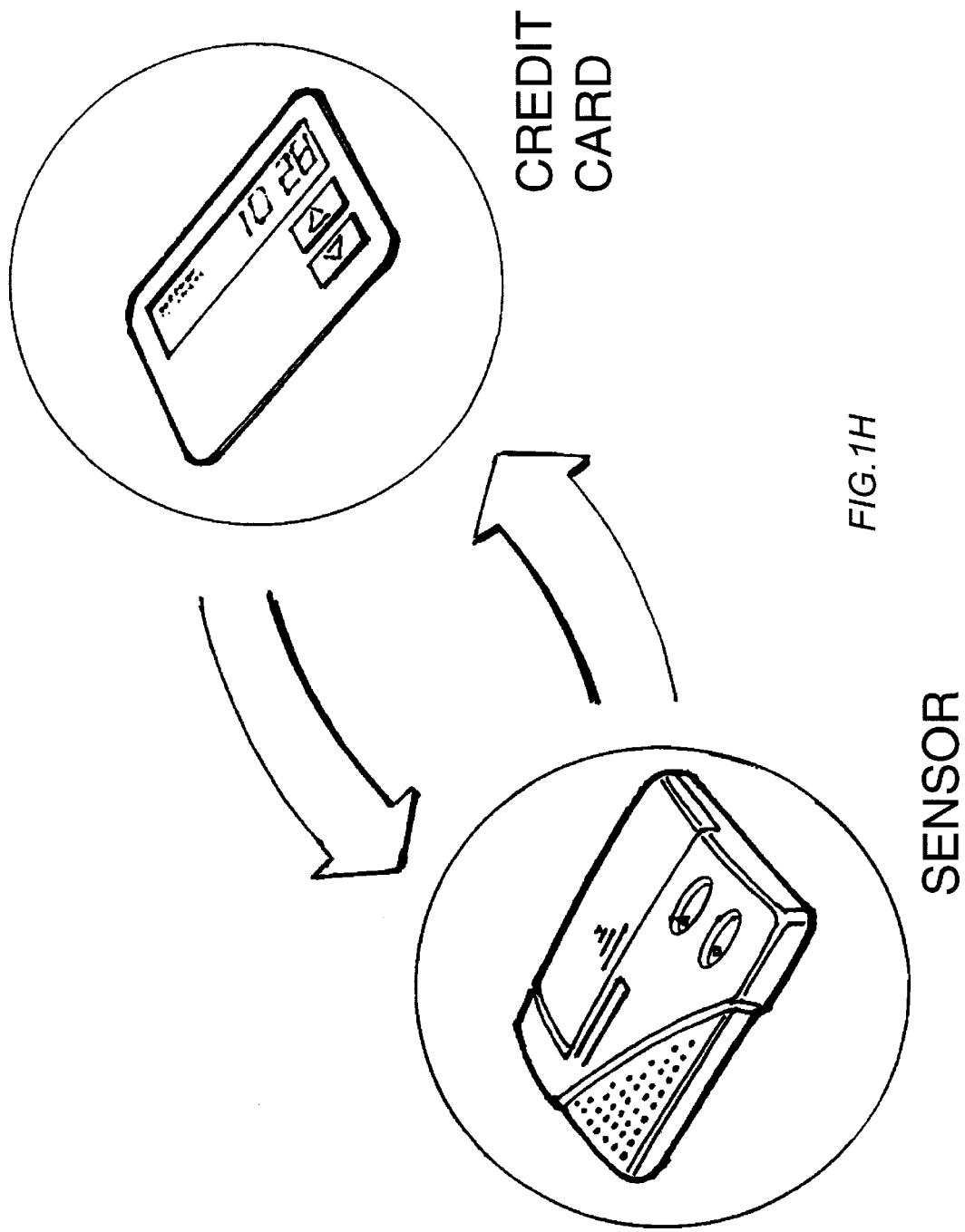

FIG. 1H shows another embodiment having bi-directional wireless communication between the sensor (first component) and user interface (second component), depicted in the Figure as a credit card-type device. Similar to the embodiment shown in FIGS. 1F and 1G, the user interface (e.g., credit card) includes buttons, microcontroller functions and, in addition, is capable of visually displaying time, date and analyte data to the user. Further, the user interface can also be designed to include other information about the user. In some embodiments, the credit card device will also be capable of sending auditory and/or tactile (e.g., vibrational) signals to the user regarding analyte data, time, etc. The sensor component is typically be placed next to the skin of the user and the credit card device worn outside in the pocket or carried in the wallet of the user.

IV. Communication Between Components

The at least two components of the present invention are preferably in operative communication with one another. The operative communication can include, for example, the following: one-way communication from the biosensor (e.g., the first component) to the user interface (e.g., a second component), or two-way communications between the first component and the second component. Communication with third or more components with either first or second component can be one-way or two-way depending on the particular type of information being communicated. Preferably, the at least two components of the monitoring system have two-way communications. Furthermore, any of the communication means (devices) described herein can be used to maintain operative communication between the at least two components and any other additional components (e.g., alarm, remote modem or PC, display, or delivery unit).

Mechanism for providing operative communication between the two components include, but are not limited to, the following:

1) One-way communication from the sensing mechanism (first component) to the display electronics (second component). The second component can include mechanism for data storage, user inputs, and the ability to upload information to a host computer.
2) Similar to (1), but with data storage, user inputs, and upload to host computer from the first component.
3) Two-way communications (send and receive) between the first and second components, where data storage, user inputs, and upload to host computer can either (a) all be in either the first or second component, or (b) split in any combination between the two sets of electronics (i.e., the first and second components).
4) (1), (2), or (3) with wireless communications link between the two components.
5) (4) with wired or wireless communications to a host device for data upload or automatic reporting to healthcare provider via telephone, internet, or wireless communications. For example, a bedside receiver that automatically reports to a patient's personal physician. This same bedside device could also function as a telephone.
6) (4) with any of the following wireless communications technologies (for example, short range communication, i.e., less than or equal to 3 meters, or longer range), including but not limited to:
   Electromagnetic waves, including but not limited to, low frequency electromagnetic waves (frequency range about 1 Hz–1 Mega Hz); medium frequency electromagnetic waves (frequency range about 1 Mega Hz–500 Mega Hz); and high frequency electromagnetic waves (frequency range about 500 Mega Hz–20 Giga Hz). Further, it is to be understood that such ranges for electromagnetic waves are approximate and may be subdivided into further categories, for example, by the FCC, which indicates that low frequency (LF) ranges between about 30 kHz and about 300 kHz; medium frequency (MF) ranges between about 300 kHz and about 3 Mega Hz (MHz); high frequency (HF) ranges between about 3 MHz and about 30 MHz; very high frequency (VHF) ranges between about 30 MHz and about 300 MHz; ultra high frequency (UHF) ranges between about 300 MHz and 3 Giga Hz (GHz); super high frequency (SHF) ranges between about 3 GHz and about 30 GHz; and extra high frequency (EHF) ranges between about 30 GHz and about 300 GHz.
   Capacitance coupling between, for example, a subject's body and the environment/air (frequency range about 1 Hz–1 Mega Hz);
   Inductive coupling (i.e., time varying magnetic field; not freely propagating electromagnetic wave);
   Close coupled inductive (i.e., inductive but so weak that it works only at very short range). This would likely require bringing the two components (e.g., a display device and sensor electronics) in close proximity whenever the data needs to be displayed;
   Brief electrical contact whenever data is needed at the display;
   Infrared coupling (using infrared light, e.g., as in low speed communications links to computers and personal digital assistants), and
   High frequency acoustic energy.
7) (5) with any of the links mentioned in (6).
8) combinations and modifications of (1)–(7), above.

Preferably, the communication between the at least two components is a wireless link. Wireless links allow for the uploading of data from the monitoring system to a personal computer or personal digital assistant (having the necessary receiver electronics) for viewing by the user, family member, medical care team or researchers. Although wire-like links can also be used for this purpose, wireless links are preferred to enhance user convenience.

A variety of approaches are available for such wireless communication including, but not limited to, electromagnetic waves such as radio frequency with carrier bands from 20 kilo Hertz to 20 Giga Hertz (see, e.g., Freiherr (1998) *Medical Device and Diagnostic Industry*, August:83–93); capacitance coupling; inductive coupling, infrared coupling, high frequency acoustic energy and frequency hopping schemes.

In one aspect, wireless communications are provided by electromagnetic waves (radio-frequency). The selection of which carrier frequency can be readily determined by one of skill in the art in view of range (e.g., distance between sensing mechanism and user interface), blocking by the human body and clothes, power consumption, bandwidth, noise susceptibility, antenna size, FCC regulations, selected communication protocol, cost and availability of starting materials. Two-way paging electronics and networks, for example RF (radio-frequency) transceivers, also find use in the present invention, for example technology manufactured and commercially available from High Desert RDN, Rupert, ID; RF Monolithics, Inc., Dallas, Tex.; and Motorola, Inc. In particular, the miniature, spread spectrum transceiver known as the RF-SOI sensor transceiver™ (High Desert RDN, Rupert, Ind.) requires less than 0.5 volts of electrical power while providing a sensor or analysis host device the ability to gather and transceive data in real time. Short-range wireless data communications are also commercially available, for example, the wireless data transceiver systems designed and available from RF Monolithics, Inc., Dallas, Tex. Two-way paging devices, e.g., ReFlex® paging hardware and service (Motorola, Inc.) are also available. These technologies can be used to transmit the data from the monitoring system to a file server (for example, a file server that is part of a wide area network (WAN) such as the internet). The information on the file server can then be readily accessed using standard web browsing software with appropriate security features implemented for confidentiality. In addition, cellular and/or cordless telephone networks can be used to transfer the data to a file server for access. See, e.g., U.S. Pat. Nos. 5,838,730 and 5,574,775. Wireless communications for local area networks (LAN) are described, for example, in U.S. Pat. Nos. 5,875,186 and 5,987,033. U.S. Pat. No. 5,077,753 and www.bluetooth.com for descriptions of Bluetooth technology, a wireless communication technology for data and voice.

In another embodiment, the wireless link (e.g., communication mechanism) is established by capacitance coupling, for example using a technology called Personal Area Network (PAN; WO 96/36134, N. Gershenfeld, et al., published Nov. 14, 1996). This technology is an example of capacitance coupling involving the use of the human body to carry current, and thus information, from one device to another. These devices have to be either in direct contact, or in close proximity, to the body. A low frequency carrier, e.g., below 1 MHz, is used to transmit the information. Advantages of PAN include that it may require less energy for data transmission, the potential of better control over security of transmitted information, and the use of simple low cost electronics.

As noted above, inductive coupling can also be used to establish wireless communication abilities between the two components of the monitoring system described herein. Inductive coupling usually requires that the communicating components be in relatively close physical proximity to each other. Suitable inductive coupling technology is described, for example, in U.S. Pat. No. 5,882,300 to Malinouskas, issued Mar. 16, 1999 directed to a wireless patient monitoring apparatus that employs inductive coupling. Wireless systems that make use of infrared coupling are also known and described, for example in U.S. Pat. Nos. 5,103,108 and 5,027,834, as are wireless communication systems that make use of high frequency acoustic energy (e.g., ultrasound). Ultrasonic wireless communications typically use frequencies between about 100 KHz and 1.0 MHz (see, e.g., U.S. Pat. No. 5,982,297).

V. Additional Components

The present invention may also include, in addition to the first and second components, other additional components, for example, additional display units, alarm mechanisms and/or delivery units such as pumps. Alarm mechanisms could be used to warn the user when the concentration of the analyte gets above or below a pre-set threshold value. In certain embodiments, the alarm will be remote from (and in communication with) the first and second components, while in other embodiments, the alarm can be included within the structure of the first or second components.

In certain embodiments, a component comprising a delivery unit capable of delivering a substance (e.g., therapeutic substance) to the subject is included in the present invention. The substance delivered to the subject will of course depend on the analyte being monitored. For instance, in the case where glucose is the analyte, the delivery unit will preferably deliver insulin. Thus, in certain embodiments, after the sampling/sensing mechanism determines the concentration of the analyte of interest, this information can be relayed to the delivery unit. Microprocessing functions within the delivery unit can then determine the appropriate amount of therapeutic substance to be delivered to the subject. Alternatively, it will be apparent that the determination of the amount of therapeutic substance to be delivered by the delivery unit can be made by any of the components of the system, for example by the first or second components following appropriate data collection and analysis. Thus, in certain embodiments, the delivery unit can be automatically controlled by the first and/or second components of the monitoring system. In addition, in some embodiments, the user can have input as to the amount of substance delivered by the delivery unit. For example, after reviewing the display of data obtained from the sampling/sensing component, the user can determine the amount of substance to be delivered and transmit appropriate instructions (e.g., via programming the microprocessing functions of the user interface) to the delivery unit. Suitable delivery units, for example, insulin pumps are described in the art. See, e.g., U.S. Pat. Nos. 5,112,614; 5,995,860; and 5,062,841. Implantable glucose monitoring-telemetry devices have also been described, see, e.g., U.S. Pat. No. 4,703,756; Atanasov et al. (1997) *Biosensors & Bioelectronics* 12:669–679; Black et al. (1996) *Sensors and Actuators* B31:147–153; McKean and Gough (1988) *IEEE Transactions on Biomedical Engineering* 35:526–532. The delivery unit may be implantable or external to the subject.

Further, it is to be understood that the present invention includes embodiments having one or more additional components (e.g., both alarm and delivery unit). It will also be apparent that the additional component(s) are preferably in operably communication with at least one of the first and second components. The nature of the communication between the additional component(s) and the first and/or second components can be readily determined by a skilled artisan using the communications mechanisms and factors described herein, for example, whether the additional component a separate structure, whether it is implanted or external, the nature of the microprocessor(s) in the components and the like. Preferably, the communication between the additional(s) components is wireless.

Figure 1I:
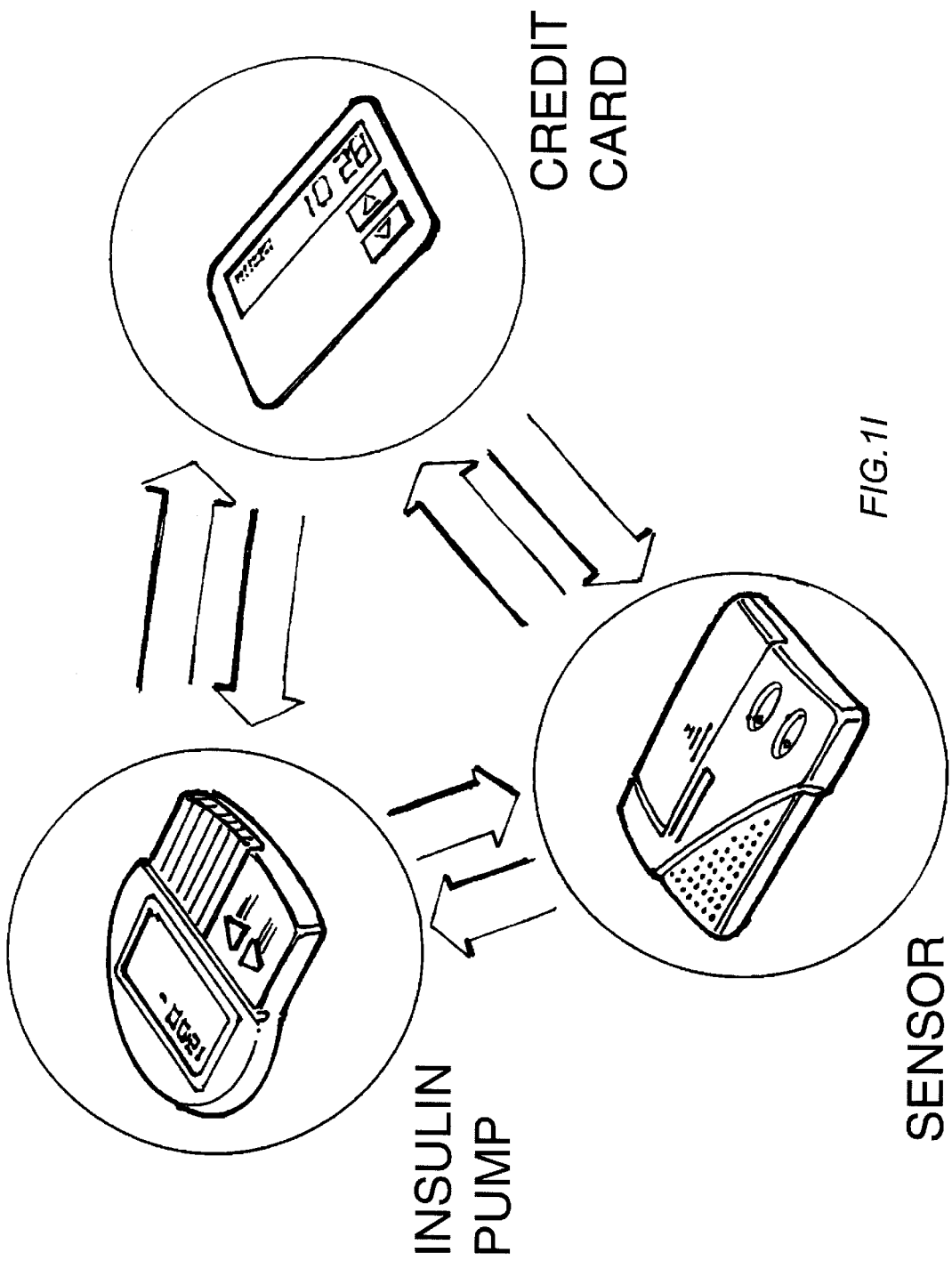

Exemplary embodiments of a monitoring system having three components are shown in FIGS. 1I to 1L. FIG. 1I depicts an embodiment of the present invention which includes three separate components: a sampling/sensing mechanism ("sensor"); a user interface (depicted as a credit card) and a drug delivery unit ("insulin pump"). As depicted in the Figure, all three components have bi-directional wireless communication abilities with each of the other elements. This allows, for example, for a feedback loop to be established between the sensor and the insulin pump without input from the user. The sensor component samples and senses the analyte (e.g., glucose) and microcontroller functions in either the insulin pump or the sensor analyze and translate the data into the amount of insulin required to be administered to the user. Further, the bi-directional wireless communication abilities also allow for situations in which the user controls the amount of insulin infused by the pump, for example, taking into account meals, exercise or other factors. As described above, the credit card can include a variety of functions (e.g., date, time, analyte data, other information) and can employ a variety of display mechanisms (e.g., visual, auditory or tactile). The sensor is preferably worn next to the skin while the credit card can be carried in a pocket or wallet. The insulin pump is preferably at least partially implanted (e.g., subcutaneously) in the user.

Figure 1J:
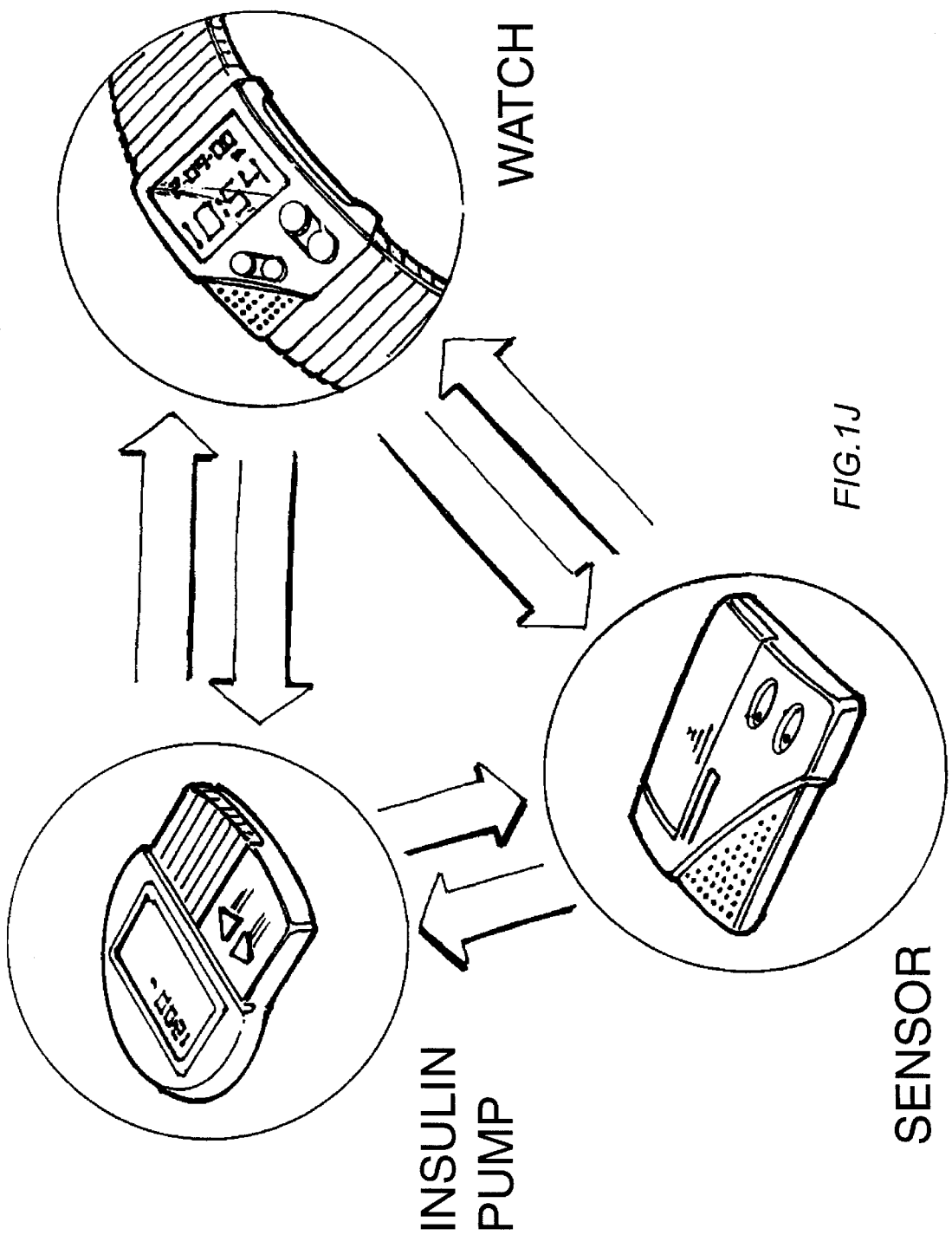
Figure 1K:
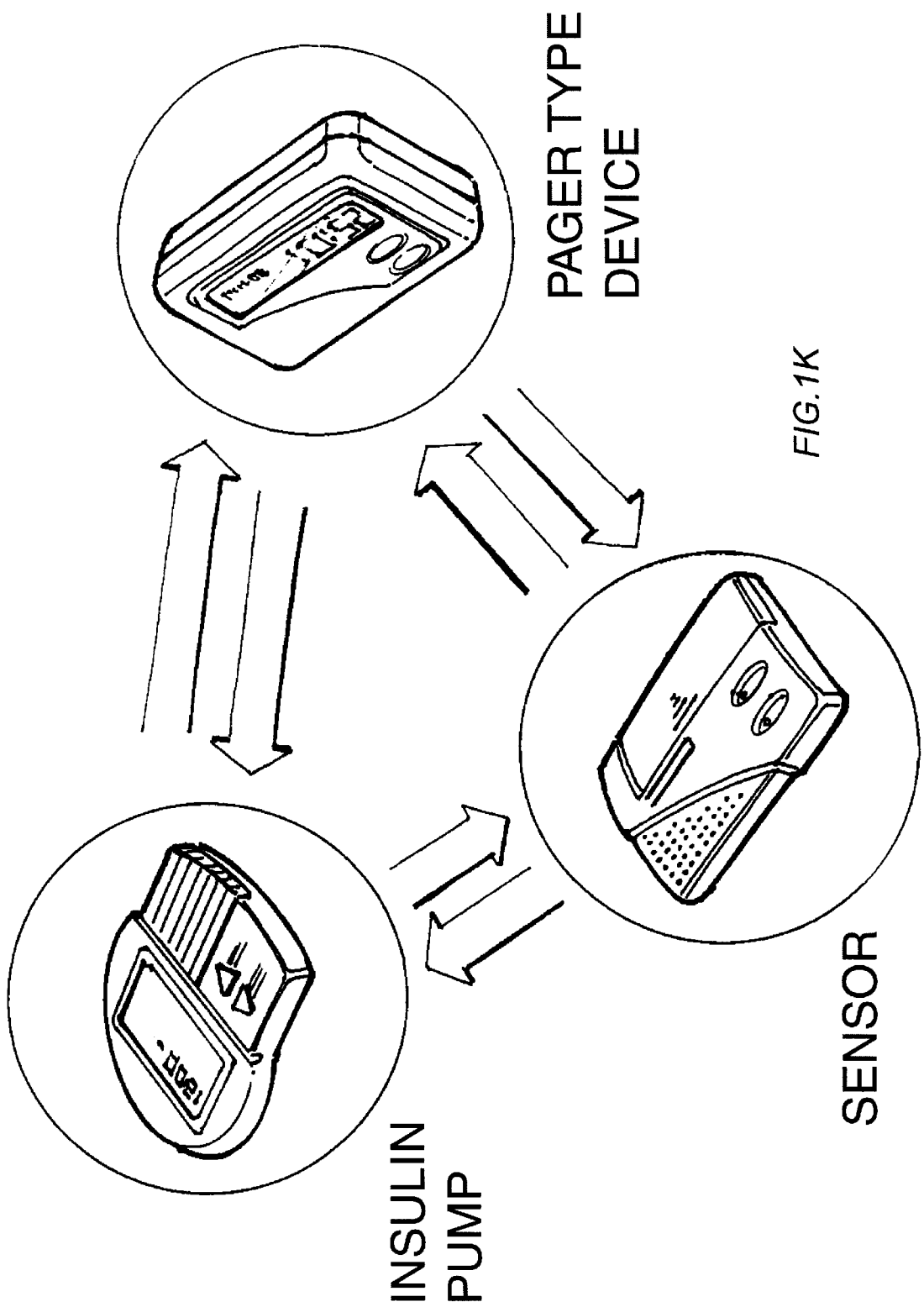

FIG. 1J depicts an embodiment similar to that of FIG. 1I except that the user interface is depicted as a watch rather than a credit card. Similarly, FIG. 1K depicts a three component, bi-directional wireless communication system as described for FIG. 1I, except that the user interface is a pager-type device.

Figure 1L:
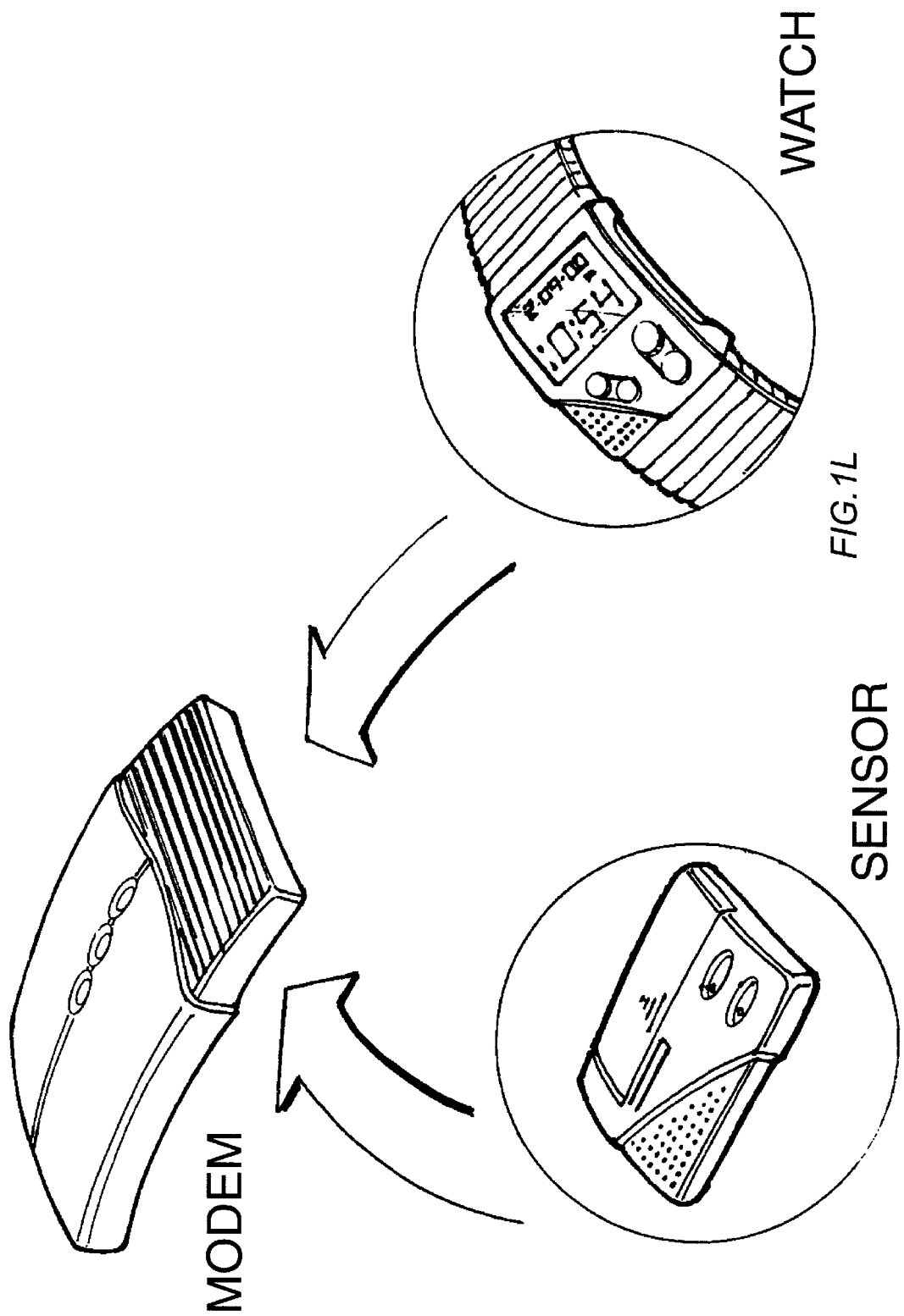

FIG. 1L depicts an embodiment of the present invention which includes three separate components: a sampling/sensing mechanism ("sensor"); a user interface (depicted as a watch) and a remote modem. As depicted in the Figure, the modem receives information from the sensor and user interface. It is to be understood that, in some embodiments, the user interface and sensor will also be in communication with one another. The presence of a remove modem allows the sharing of data between the user and variety of other interested parties. For example, the modem can be linked to a wide area network (WAN) such as the internet and transmitted to secure file server for accessed using, for example, web browsing software (with appropriate security measures) by a doctor or hospital personnel. As described above, the watch can include a variety of functions (e.g., date, time, analyte data, other information) and can employ a variety of display mechanisms (e.g., visual, auditory or tactile). The sensor is preferably worn next to the skin while the watch is worn on the wrist.

Although preferred embodiments of the subject invention have been described in some detail, it is understood that obvious variations can be made without departing from the spirit and the scope of the invention as defined by the appended claims.

What is claimed is:

1. A monitoring system for frequently measuring glucose present in a subject and providing to said subject self-monitoring of said glucose, said monitoring system comprising,
   (A) a first component to be placed in contact with a skin or mucosal surface of said subject comprising
       (i) an iontophoretic sampling mechanism for extracting the glucose from the subject, wherein said sampling mechanism is adapted for extracting the glucose across the skin or mucosal surface of said-subject;
       (ii) a sensing mechanism in operative contact with the glucose extracted by the sampling mechanism, wherein said sensing mechanism obtains a signal from the extracted glucose by detecting electrochemical signals produced at a biosensor electrode surface and said signal is specifically related to the glucose amount or concentration; and
       (iii) a first mechanism for providing operative communication with a second component of the monitoring system, wherein said operative communication comprises wireless communication technology that employs electromagnetic waves;
   wherein said first and second components are separately housed; and
   (B) the second component, comprising
       (i) a user interface;
       (ii) a second mechanism for providing operative communication with the first component, wherein said operative communication comprises wireless communication technology that employs electromagnetic waves, the second component (a) receives the signal from the first component, and (b) is capable of communicating with a third component remote from the subject being monitored, and
       (iii) a computing mechanism that converts the signal from the extracted glucose to an output indicative of the amount or concentration of glucose extracted by the sampling mechanism, wherein the second component displays said output and provides an alarm to the subject when the amount or concentration of glucose is above or below threshold values;
   wherein said second component is adapted to be carried by the subject.

2. The monitoring system of claim 1, wherein the wireless communication technology employs low frequency electromagnetic waves in a frequency range of about 1 Hz. to about 1 Mega Hz.

3. The monitoring system of claim 1, wherein the wireless communication technology employs medium frequency electromagnetic waves in a frequency range of about 1 Mega Hz. to about 500 Mega Hz.

4. The monitoring system of claim 1, wherein the wireless communication technology employs high frequency electromagnetic waves in a frequency range of about 500 Mega Hz. to about 5 Giga Hz.

5. The monitoring system of claim 1, wherein the second component relays command signals to the first component.

6. The monitoring system of claim 5, wherein the command signals include signals to control operation of the sensing mechanism.

7. The monitoring system of claim 5, wherein the command signals include signals to control operation of the sampling mechanism.

8. The monitoring system of claim 1, wherein the second component can store glucose-related data.

9. The monitoring system claim 1, wherein said subject is a mammal.

10. The monitoring system of claim 9, wherein said mammal is a human.

11. The monitoring system of claim 1, further comprising
    (C) a delivery device component comprising
        (i) a delivery device; and
        (ii) a third mechanism for providing operative communication with the first and second components, wherein the communication between first and second components and the third component is wireless.

12. The monitoring system of claim 11, wherein the delivery device is implanted in the subject.

13. The monitoring system of claim 11, wherein the delivery device is external to the subject.

14. The monitoring system of claim 11, wherein the delivery device comprises an insulin pump.

15. The monitoring system of claim 1, further comprising
    (C) the third component comprising
        (i) a modem or personal computer; and
        (ii) a third mechanism for providing operative communication with the first and second components, wherein said operative communication comprises wireless communication technology that employs electromagnetic waves.

16. The monitoring system of claim 15, wherein the modem or personal computer is operably linked to a wide area network (WAN).

* * * * *

UNITED STATES PATENT AND TRADEMARK OFFICE
CERTIFICATE OF CORRECTION

PATENT NO. : 6,561,978 B1
DATED : May 13, 2003
INVENTOR(S) : Thomas E. Conn et al.

It is certified that error appears in the above-identified patent and that said Letters Patent is hereby corrected as shown below:

Column 21,
Line 18, "surface of said-subject;" should be -- surface of said subject; --.

Signed and Sealed this

First Day of July, 2003

JAMES E. ROGAN
*Director of the United States Patent and Trademark Office*